United States Patent
Woodruff et al.

(10) Patent No.: US 6,461,351 B1
(45) Date of Patent: Oct. 8, 2002

(54) ENERGY DELIVERY SYSTEM AND METHOD FOR PERFORMING MYOCARDIAL REVASCULARIZATION

(75) Inventors: Eileen A. Woodruff, Whitinsville; Robert R. Andrews, Norfolk; Richard Yeomans, Medway; Stephen J. Linhares, Taunton; Robert I. Rudko, Holliston, all of MA (US)

(73) Assignee: PLC Medical Systems, Inc., Franklin, MA (US)

( * ) Notice: Subject to any disclaimer, the term of this patent is extended or adjusted under 35 U.S.C. 154(b) by 25 days.

(21) Appl. No.: 09/687,924

(22) Filed: Oct. 13, 2000

Related U.S. Application Data

(62) Division of application No. 09/263,977, filed on Mar. 5, 1999, now Pat. No. 6,287,297.

(51) Int. Cl.[7] ............................................. A61B 18/04
(52) U.S. Cl. ........................ 606/32; 606/41; 606/45; 606/47; 607/9; 600/16; 600/17
(58) Field of Search .................................. 606/7, 13–16, 606/41, 45–49, 32–36; 607/9–11; 600/16–18; 128/898

(56) References Cited

U.S. PATENT DOCUMENTS

| 5,125,926 A | 6/1992 | Rudko et al. ............... 606/19 |
| 5,370,675 A | 12/1994 | Edwards et al. ............ 607/101 |
| 5,389,096 A | 2/1995 | Aita et al. ................. 606/15 |
| 5,403,311 A | 4/1995 | Abele et al. ............... 606/49 |
| 5,441,499 A | 8/1995 | Fritzsch .................... 606/45 |
| 5,554,152 A | 9/1996 | Aita et al. ................. 606/7 |
| 5,607,421 A | 3/1997 | Jeevanandam et al. ....... 606/15 |
| 5,672,170 A * | 9/1997 | Choe et al. ................. 606/12 |
| 5,683,366 A | 11/1997 | Eggers et al. .............. 604/114 |
| 5,725,521 A | 3/1998 | Mueller ...................... 606/7 |
| 5,759,158 A * | 6/1998 | Swanson .................... 600/508 |
| 5,769,843 A | 6/1998 | Abela et al. ............... 606/10 |
| 5,807,384 A | 9/1998 | Mueller ...................... 606/7 |
| 5,807,388 A | 9/1998 | Jeevanandam et al. ....... 606/15 |
| 5,824,005 A | 10/1998 | Motamedi et al. ........... 606/15 |
| 5,860,951 A | 1/1999 | Eggers et al. .............. 604/49 |
| 5,873,865 A * | 2/1999 | Horzewski et al. ........ 604/280 |
| 6,023,638 A * | 2/2000 | Swanson .................... 600/510 |
| 6,030,377 A | 2/2000 | Linhares et al. ............. 606/7 |
| 6,032,674 A * | 3/2000 | Eggers et al. ............. 128/898 |
| 6,156,029 A * | 12/2000 | Mueller ...................... 606/7 |
| 6,171,251 B1 * | 1/2001 | Mueller et al. ............. 600/481 |
| 6,241,665 B1 * | 6/2001 | Negus et al. ............... 600/374 |

FOREIGN PATENT DOCUMENTS

| DE | 296 09 350 A | 10/1996 |
| WO | WO 98/25533 | 6/1998 |
| WO | WO 98/27877 | 7/1998 |

* cited by examiner

Primary Examiner—Linda C. M. Dvorak
Assistant Examiner—Ahmed Farah
(74) Attorney, Agent, or Firm—Fish & Richardson P.C.

(57) ABSTRACT

An energy delivery system for performing myocardial revascularization on a heart of a patient including an energy pulse source that produces energy pulses sufficient to create channels in a wall of a heart, and an energy pulse delivery system connected to receive the energy pulses and deliver the energy pulses to desired locations for channels in the wall of the heart. Also disclosed are a sensor that senses a cyclical event related to the contraction and expansion of the beating heart; a controller responsive to the sensor for automatically firing the energy pulse system to provide energy to strike the beating heart only within a safe time period during a heart beat cycle; RF electrical or laser energy pulses; a temperature sensor to avoid damage caused by overheating adjacent heart tissue; a thermal conductivity cooling system; and programmably adjusting duty cycle, duration and amplitude of energy pulses.

16 Claims, 14 Drawing Sheets

ECG WAVEFORM

ENERGY DELIVERY SYSTEM AND METHOD FOR PERFORMING MYOCARDIAL REVASCULARIZATION

This application is a divisional of U.S. application Ser. No. 09/263,977, filed Mar. 5, 1999, now U.S. Pat. No. 6,287,297.

BACKGROUND OF THE INVENTION

The invention relates to an energy delivery system for performing myocardial revascularization on a beating heart of a patient.

Transmyocardial revascularization (TMR) is a surgical treatment for cardiovascular disease. Present TMR procedure is an open chest technique (thoracotomy) that uses a laser beam to drill holes through the myocardium, typically into the left ventricle. These holes or channels extend through the entire heart wall thickness from the outside through to the ventricle. The openings of the channels on the outside surface of the heart heal due to external pressure from the surgeon, but the channels are believed to remain open on the inside, allowing blood to enter the heart wall tissue from the ventricle.

In another approach myocardial revascularization can be performed using a catheter introduced percutaneously so that the tip of the catheter is inside a chamber of the heart, typically the left ventricle, where the holes or channels can be created from the inside toward but not through the outside of the heart. This approach is also known as endocardial laser revascularization (ELR), percutaneous myocardial revascularization (PMR), and direct myocardial revascularization (DMR). The channels are drilled with a laser beam introduced through the catheter.

Certain problems are presented when laser revascularization is done on a beating heart. A beating heart presents a moving target, which can make it difficult to accurately and consistently form channels of a desired depth and size. The heart also is extremely sensitive to a laser pulse at certain times during its cycle. A laser pulse striking the heart at the T time of an electrocardiogram (ECG) signal could cause the heart to fibrillate and result in heart failure. While one could stop the heart during the process of TMR, this poses other risks to the patient and complicates the operating procedure. The heart must be cooled and the patient connected to a heart-lung machine.

However, the risk of inducing a beating heart to fibrillate is greatly reduced when the laser is fired only during the refractory period of the heart cycle between the R and T waves of the ECG signal. An additional benefit of firing the laser only between the R and T waves is that this is the period of the heartbeat cycle during which the heart is most still and channels can be formed most accurately. Rudko U.S. Pat. No. 5,125,926 describes a heart-synchronized pulsed laser system that fires a laser only during the refractory period of the heartbeat cycle. The patent describes an open chest procedure using an articulated optical arm or a fiber optic element to deliver the laser beam to a surface of the heart.

Aita U.S. Pat. No. 5,389,096 discloses a percutaneous TMR procedure in which a steerable heart catheter is guided from the femoral artery via the abdominal artery into the left ventricle. The laser energy is delivered through the working channel of the catheter by a fiber optic delivery system.

WO 98/27877 and Eggers U.S. Pat. No. 5,860,951 describe using electrical current pulses delivered from electrodes on a catheter (for percutaneous access) or handpiece (for external access) to create channels in a TMR procedure.

The above-referenced patents and PCT publication are hereby incorporated by reference in their entireties.

SUMMARY OF THE INVENTION

In one aspect, the invention features, in general, a heart-synchronized energy delivery system for performing myocardial revascularization on a beating heart of a patient. The system includes an energy pulse source that produces electrical pulses sufficient to create channels in a wall of the heart, an energy pulse source delivery system (e.g., a handpiece or catheter with an electrode for delivering the pulses to a heart wall surface), a heart cycle sensor, and a controller that is responsive to the heart cycle sensor for firing the energy pulse system to provide energy to strike the beating heart only within a safe time period during a heart beat cycle. The safe time period is automatically determined by the controller with respect to the cyclical event.

In another aspect, the invention features, in general, an energy delivery system for performing myocardial revascularization on a heart of a patient. The system includes an energy pulse source that produces electrical pulses and an energy pulse delivery system that includes a support structure that is expandable from a retracted position in a catheter to an expanded position in which the structure has portions adjacent to a plurality of locations on an interior surface of a wall of a chamber of the heart. The support structure carries a plurality of electrodes that deliver electrical pulses to respective locations on the wall of the heart to form respective channels in the wall of the heart.

In another aspect, the invention features, in general, an energy delivery system for performing myocardial revascularization. The system includes an energy pulse source that produces electrical pulses, and an energy pulse delivery system that has an electrode for delivering the electrical pulses to a desired location for a channel in the wall of the heart of a patient. The system also includes an electromotion mechanism for advancing the electrode into the channel as, or shortly after but not before, the channel regions are formed. The mechanism also retracts the electrode from the channel that has been formed.

In another aspect, the invention features, in general, an energy delivery system for performing myocardial revascularization. The system includes an energy pulse source and an energy pulse delivery system with a delivering end for delivering the energy pulses to desired locations for channels in the wall of a heart of a patient. The system may also include a temperature sensor sensing temperature of the delivery end or of the heart wall during creation of a channel, and the energy pulse source is responsive to the temperature in controlling the production of energy pulses.

In another aspect, the invention features, in general, an energy delivery system for performing myocardial revascularization on a heart of a patient. The system includes an energy pulse source and an energy pulse delivery system for delivering energy pulses to create channels in a wall of a heart of a patient. The system also includes a cooling system that via thermal conductivity removes heat generated during creation of channels in the heart of a patient.

In another aspect, the invention features, in general, an energy delivery system for performing myocardial revascularization including an energy pulse source that produces energy pulses sufficient to create channels in a wall of the heart, and an energy pulse delivery system for delivering the energy pulses to desired locations for channels in a wall of a heart. The energy pulse source programmably varies duty cycle, amplitude, and duration of the energy pulses. The flow rate of a cooling system or temperature of a cooling substance could also be adjusted.

In another aspect, the invention features, in general, an energy delivery system for performing myocardial revascularization on a heart of a patient. The system includes an energy pulse source and an energy pulse delivery system for delivering energy pulses to create channels in a wall of a heart of a patient. The system also includes a sensor (e.g., an ultrasound sensor) that senses a dimension of the myocardium of the heart (e.g., its thickness or the depth of a channel being formed), and the energy pulse source and the energy pulse delivery system are responsive to the sensor to control the formation (e.g., the depth) of the channel.

In other aspects of the invention, the invention features, in general, a heart-synchronized energy delivery system for performing myocardial revascularization on a beating heart of a patient the includes a heart cycle sensor that senses blood pressure, ventricular contraction, or acoustics related to ventricular contraction. Blood pressure measurements include ventricular, atrial, aortic, and pulminary artery/pulminary capillary wedge pressures.

Particular embodiments of the invention may include one or more of the following features. The electrical pulses are pulses of alternating current, preferably radio frequency or microwave. The support structure for multiple electrodes is a spiral or is basket shaped. A single pulse or a plurality of pulses are used to create each channel, and the electromotion mechanism advances each electrode between or within the pulses. The heart cycle sensor senses an electrical signal (e.g., a standard or local ECG signal or a pacemaker signal) that causes the heart to beat. The safe time period is a period in which firing of the energy pulse system will not cause fibrillation of the heart. The safe time period is a period during which the heart is less sensitive electrically. The energy pulse system controller includes an operator input device (e.g., a foot actuated switch) that provides an activation signal to activate firing of the energy pulse system, and the energy pulse system controller fires the energy pulse system during the safe time period subsequent to receiving the activation signal. The energy pulse delivery system includes a handpiece having an end adapted to contact the outside surface of a wall of the heart. Alternatively the energy pulse delivery system delivers the energy pulses to an inside surface of a wall of the heart, via an energy conduit. The energy conduit may consist of an electrically conductive probe and wire connected to the probe. The probe may be made of beryllium copper or another conductive material. The wire may be constructed of kink resistant material such as a superelastic alloy, for example, Nitinol.

The invention also includes methods of performing myocardial revascularization relating to the aspects and features of the invention described above.

Embodiments of the invention may include one or more of the following advantages. Fibrillation is avoided by operating only within a safe time period. In addition, the energy pulses can be desirably applied to the heart when it is relatively immobile to promote accuracy. The heart cycle can desirably be determined by monitoring one of a variety of different parameters. A plurality of channels can be provided at one time, reducing the time of the procedure and stress on the patient. The delivery of energy pulses and the rate of advancement can or may be programmably controlled to provide optimal conditions and avoid thermal and/or mechanical damage to the heart tissue. A temperature sensor can sense either the temperature of a probe or the temperature of tissue surrounding the channel being formed and the procedure can be controlled to avoid heat caused tissue damage. The temperature of the probe can be lowered and maintained using an integral cooling system and adjustment of energy parameters that may include amplitude, duration, and duty cycle.

Other advantages and features of the invention will be apparent from the following description of particular embodiments of the invention and from the claims.

DETAILED DESCRIPTION OF PARTICULAR EMBODIMENTS

Figure 1:
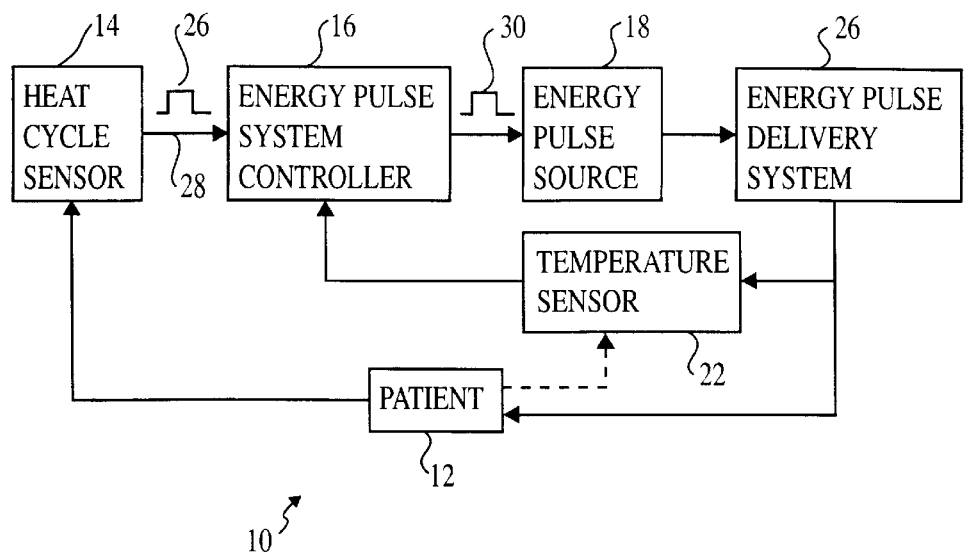
FIG. 1 is a block diagram of an energy delivery system for performing myocardial revascularization.

Referring to FIG. 1, there is shown system 10 for delivering energy pulses to patient 12 to perform myocardial revascularization on a beating heart of patient 12. System includes heart cycle sensor 14, energy pulse system controller 16, energy pulse source 18, energy pulse delivery system 20, and temperature sensor 22. Temperature sensor 22 senses the temperature of a delivery component of energy pulse delivery system 20 or the temperature of the patient's tissue to avoid heat damage to adjacent tissue.

Heart cycle sensor 14 can be a standard ECG monitor with external electrodes (see ECG diagram in FIG. 10), a local ECG monitor having electrodes that directly contact the heart of patient 12 (see FIGS. 5A–5D), an input from a pacemaker that is pacing the heart of patient 12, a pressure sensor that senses the patient's blood pressure (e.g., a sensor in lumen 24, FIG. 5; see pressure diagram in FIG. 11), an electrical impedance, e.g., strain gauge type, sensor (see FIGS. 5E'5F) that directly senses ventricular contraction (see ventricular contraction diagram in FIG. 12), an acoustic sensor (see FIGS. 5G and 5H) that senses an acoustical signal that varies as a function of ventricular contraction (see FIG. 10A), or any other sensor that senses a cyclical event related to the contraction and expansion of the beating heart.

Energy pulse system controller 16 receives an event signal 26 on line 28 from heart cycle sensor 14 and provides a synchronization signal 30 to energy pulse source 18. Energy pulse system controller 16 could, e.g., be of the type described in U.S. Pat. No. 5,125,926, which is hereby incorporated by reference. Synchronization signal 30 could be a pulse, as shown, with a leading edge indicating the beginning of a safe period for applying energy pulses to the patient's heart and a trailing edge indicating the end of the safe period. Alternatively, two pulses could be used on one or more lines, one indicating the beginning and one indicating the ending. Signal 30 might also merely indicate a beginning time, with an ending time being determined by some other means or technique. Energy pulse system controller 16 can be implemented by a host computer, a microprocessor, hardwired logic circuits, or some combination of two or all three. It can include operator input devices, including a keyboard, mouse, and foot actuated switch, as described in U.S. Pat. No. 5,125,926.

Energy pulse source 18 can be a laser firing circuit and laser, as described in U.S. Pat. No. 5,125,926, a different type of laser firing circuit and laser (e.g., as described in U.S. Pat. No. 5,389,096), or a source of another type of energy, such as electrical current pulses (e.g., as described in WO 98/27877) or an AC voltage or current of a given amplitude, frequency, and duty cycle.

Figure 7:
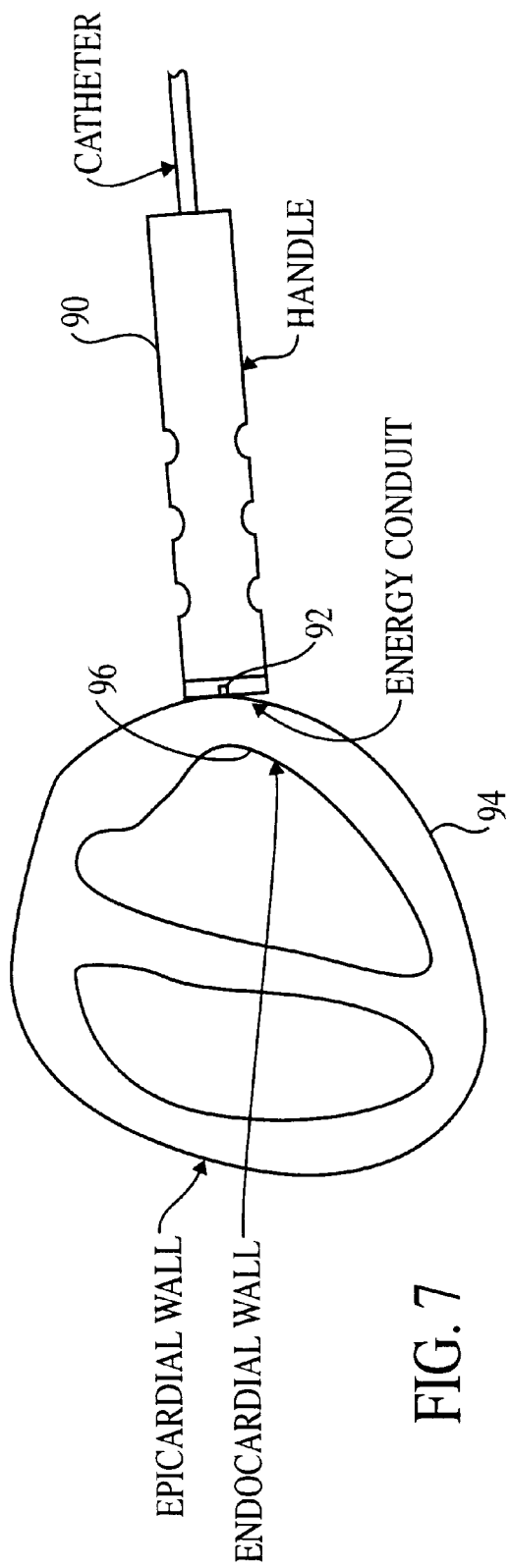
FIG. 7 is an illustration showing an RF or microwave myocardial handpiece in position on the outside of a patient's heart.

Energy pulse delivery system 20 can include a catheter (e.g., FIGS. 3 and 4; see also WO 98/27877) used to percutaneously deliver energy pulses to an interior surface of a heart wall or a handpiece (e.g., FIG. 7 or as described in U.S. application Ser. No. 08/190,950, filed Feb. 3, 1994, which is hereby incorporated by reference) to deliver pulses to an exterior surface of a heart wall through an incision in the patient's chest. Energy pulse delivery system 20 also includes optical fibers or other optics in the case of laser pulses, or electrical conductors in the case of electrical pulses.

Figure 2:
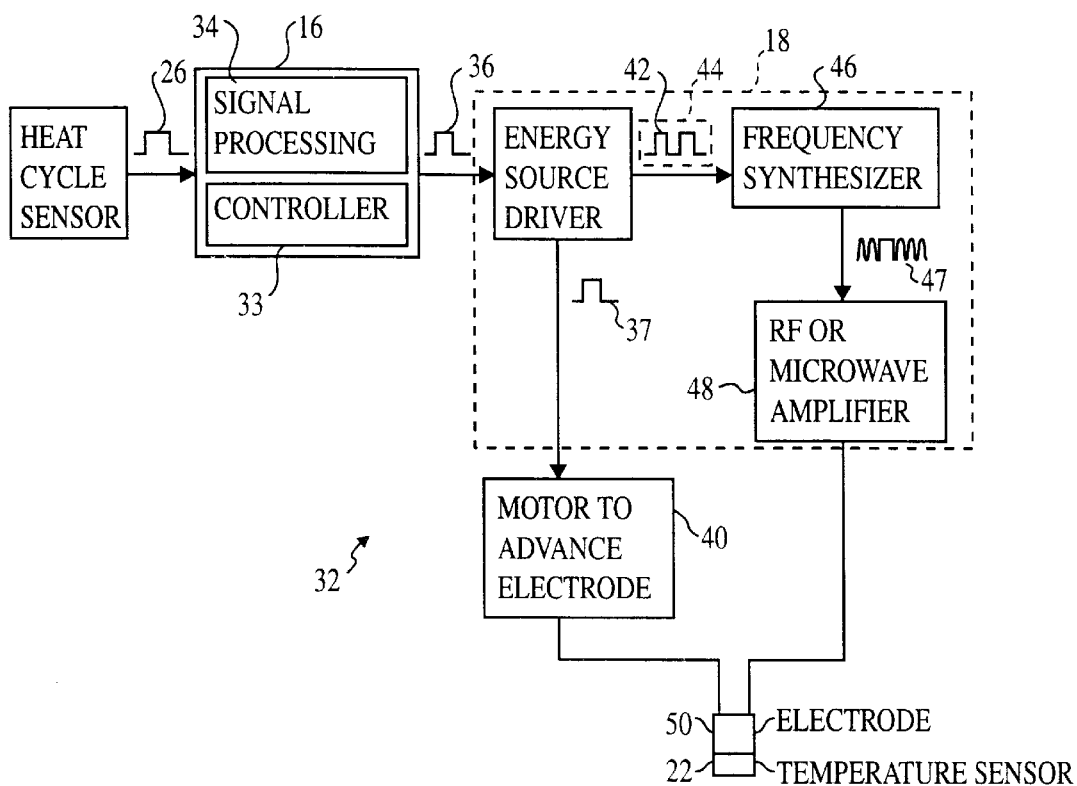
FIG. 2 is a block diagram showing an RF or microwave energy delivery system for performing myocardial revascularization.

FIG. 2 shows the components of energy pulse system 32 for delivering RF or microwave electrical pulses to a patient's heart to create channels for myocardial revascularization. System 32 includes a controller 33 that provides a user interface (including display and input devices) and provides overall control for the operation of the other components shown on FIG. 2; controller 33 can be implemented by a host computer, a microprocessor, hardwired logic circuits, or some combination of two or all three. In addition, some of the other components shown on FIG. 2 could be implemented by appropriate programming of the same computer or microprocessor, or there could be multiple computers for implementing controller 33 and/or other components, e.g., in a networked control environment. Energy pulse system controller 16 of FIG. 1 is implemented by signal processing circuit 34 of FIG. 2. Circuit 34 receives an input from an ECG monitor and provides synchronization pulse 36 to energy source driver 38. Driver 38 provides a motor control signal 37 used to control motor 40, which advances RF or microwave probe 50 into a channel being formed. Driver 38 also provides pulse signals 42 within safe time window 44 to frequency synthesizer 46. Motor control signal 37 could be delayed slightly with respect to the beginning of the delivery of energy pulses and could end at the same time that the energy pulses end.

The output 47 of frequency synthesizer 46 is amplified at RF or microwave amplifier 48 and provided to RF or microwave probe 50, which could be a handpiece (for delivery to an exterior surface) or a catheter (for delivery to an interior heart surface). Probe 50 carries temperature sensor 22. Motor 40 and probe 50 are included in the energy pulse delivery system 20 shown in FIG. 1.

Figure 3:
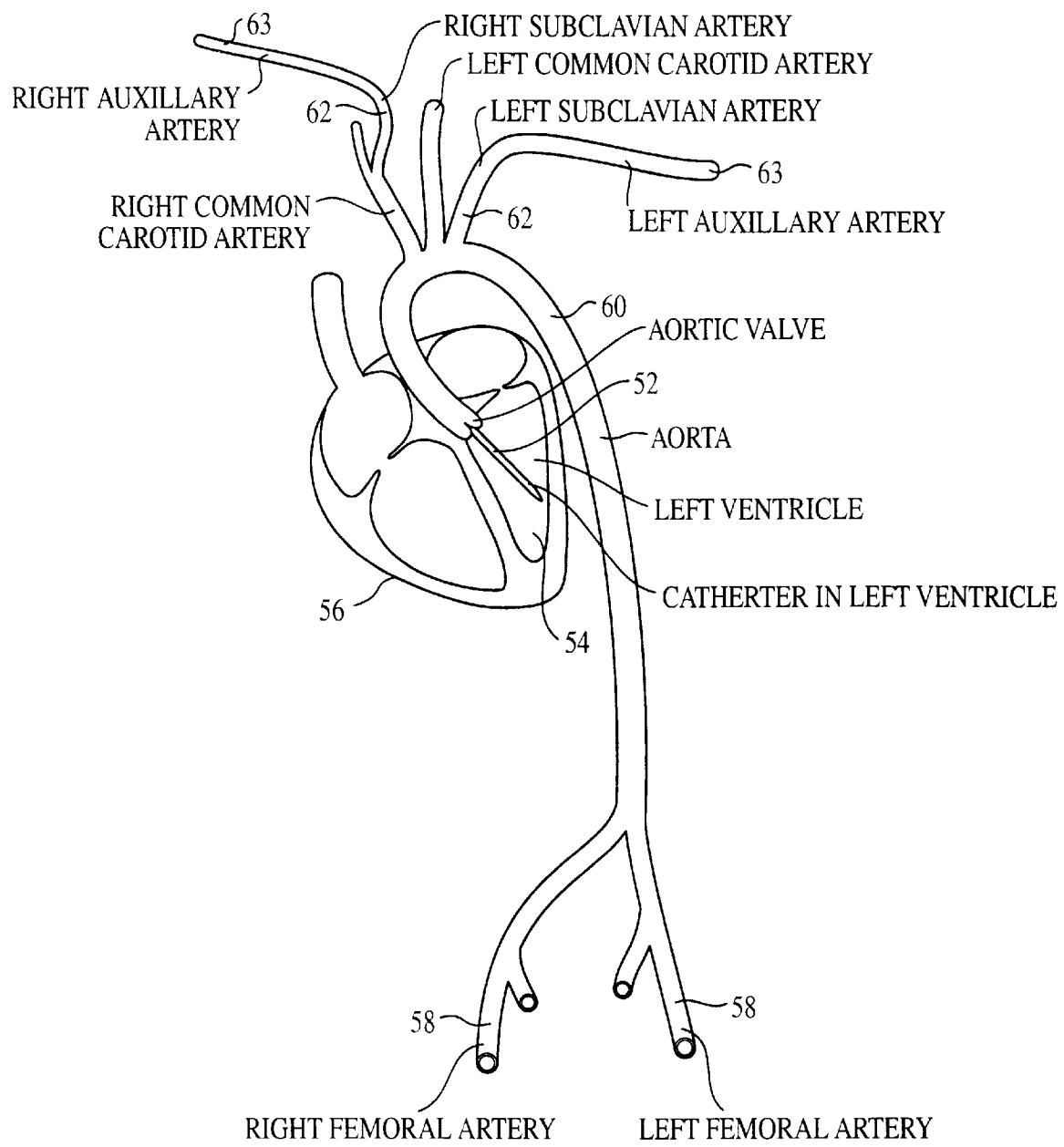
FIG. 3 is an illustration showing a percutaneously introduced myocardial revascularization catheter in a patient's heart.

FIG. 3 shows catheter 52 (used to deliver energy pulses) in the left ventricle 54 of patient's heart 56. The catheter can be directed to the heart through various access points in the patient's blood vessels. These include the typical insertion into one of the femoral arteries 58, antigrade insertion directly into aorta 60, subclavian insertion through subclavian artery 62, or transaxillary insertion through the left or right auxiliary artery 63.

Figure 4:
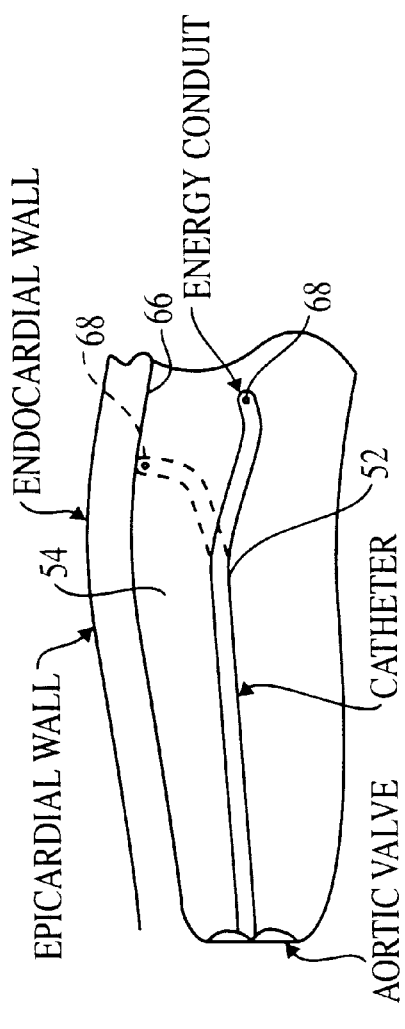
FIG. 4 is an illustration showing an a myocardial revascularization catheter in a chamber of a patient's heart.

FIG. 4 shows the end of catheter 52 in the middle of the left ventricle (in solid lines) and in a deflected position contacting the enndocardial wall 66 in position to create a channel. As is known in the art, catheter 52 includes internal wires that are controlled by actuators outside of the patient so as to bend and steer the end in the desired direction. In the embodiment shown in FIG. 4, catheter 52 carries energy conduit 68, which can be an RF or microwave delivery needle or electrode 68 with one or more electrodes at its tip for delivering RF or microwave pulses. If laser pulses were being delivered instead, catheter 52 would contain internal optical fibers, and energy conduit 68 would be terminal optics.

Figure 5:
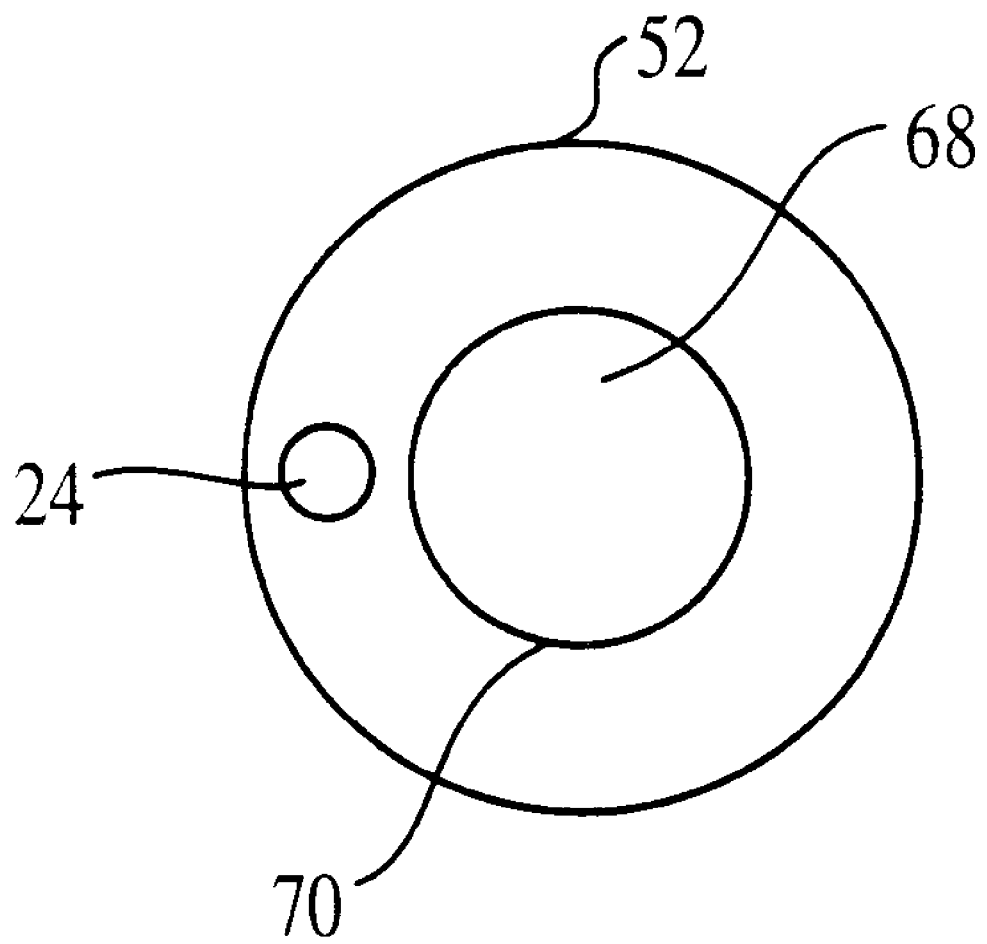
FIG. 5 is a diagrammatic end view of the end of a myocardial revascularization catheter having a pressure sensing lumen.
Figure 5B:
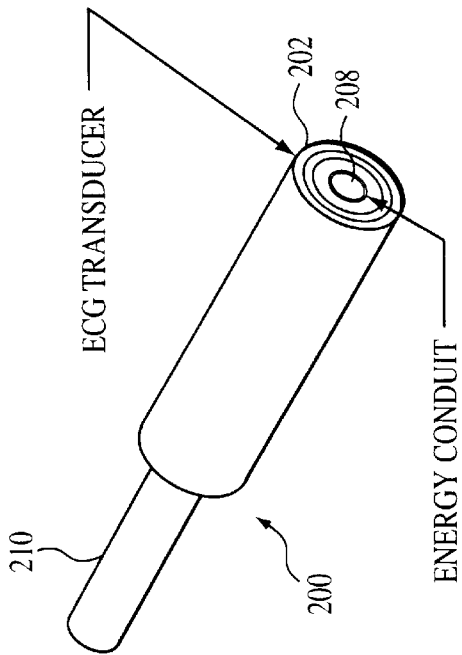
FIGS. 5A–5D are a sectional view, perspective view, and elevations, respectively, showing placement of local ECG transducers on a myocardial revascularization catheter.
Figure 5D:
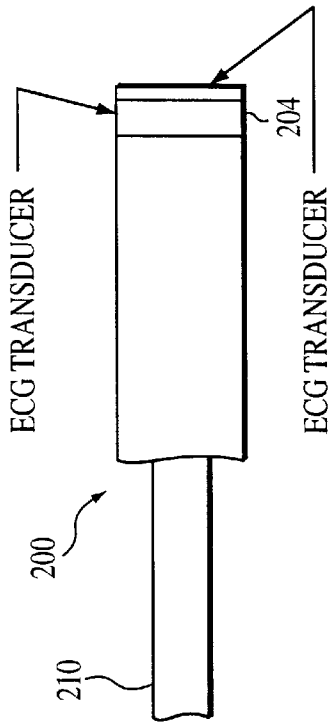
Figure 5A:
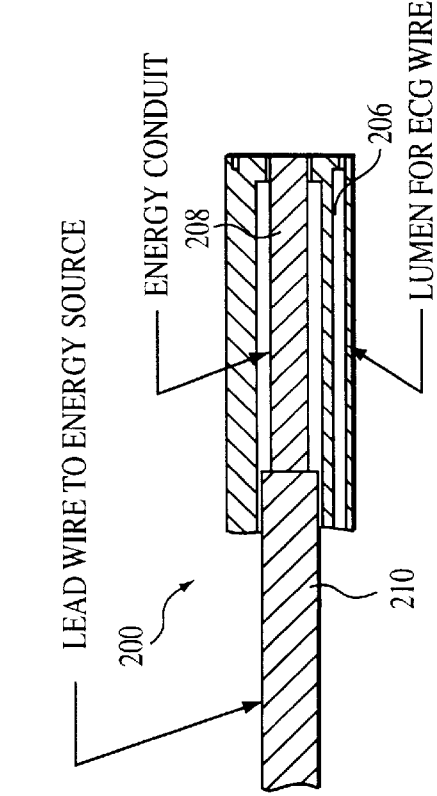
Figure 5C:
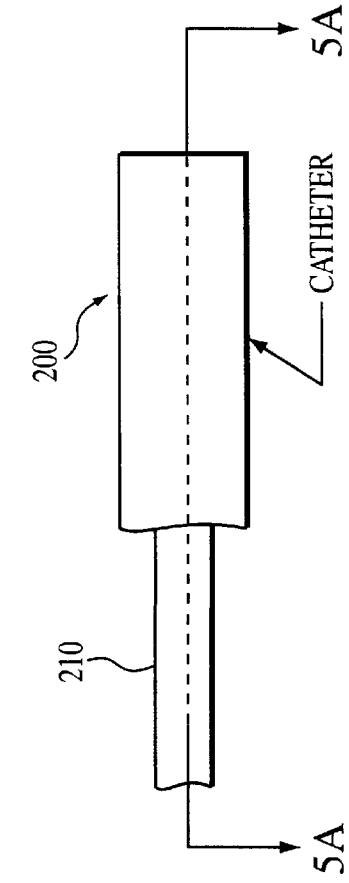

FIG. 5 shows an end view of catheter 52. It is seen that catheter 52 has a delivery lumen 70 for energy conduit 68 and a pressure sensing lumen 24 communicating with a pressure sensor. Energy conduit 68 is connected to be advanced by motor 40 of FIG. 2 as a channel is created in a patient's heart.

FIGS. 5A–5D show catheter 200 with ECG transducers 202, 204 for directly contacting the heart (inside or outside) and obtaining a local ECG signal for use in synchronization. Catheter 200 also includes lumen 206 for ECG wires, energy conduit 208, and a wire 210 (alternatively optical fibers could be used for laser pulses) for connection to the rest of the energy pulse delivery system.

Figure 5E:
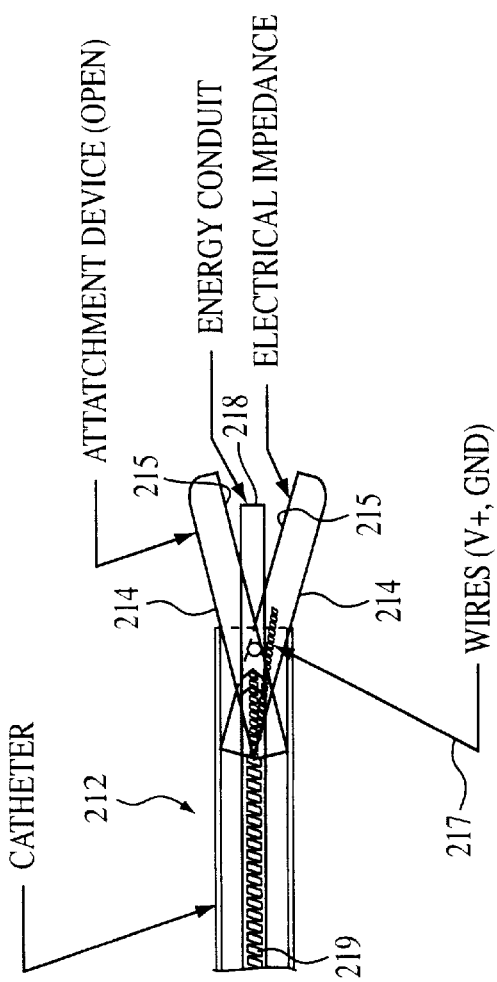
FIG. 5E is a diagrammatic elevation of a myocardial revascularization catheter having a heart contraction sensor mounted on a catheter.
Figure 5F:
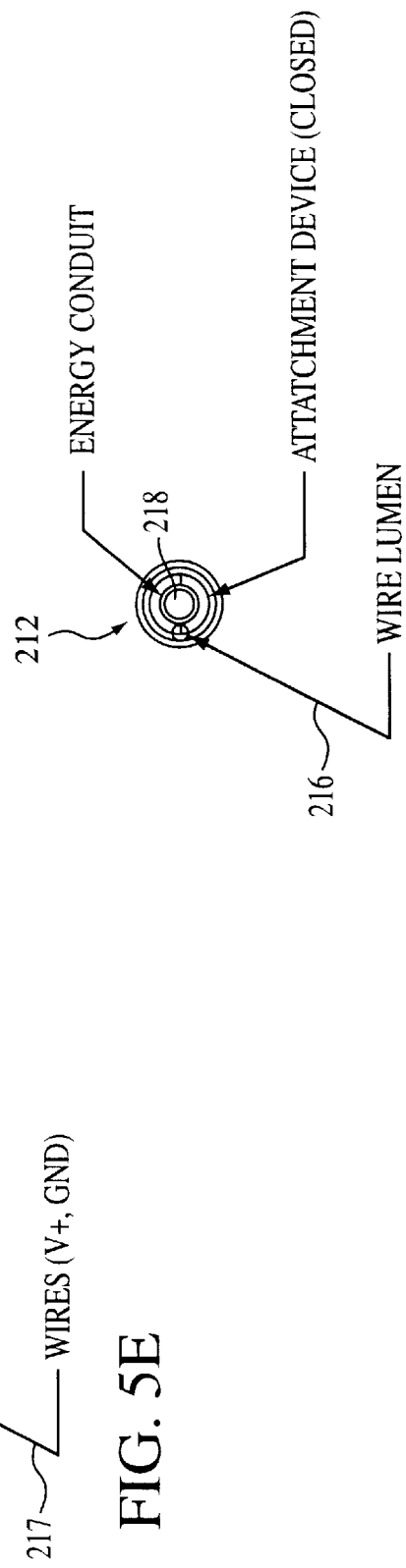
FIG. 5F is an end view of the FIG. 5E myocardial revascularization catheter in a different position.

FIGS. 5E–5F show catheter 212 with attachment jaws 214, and a strain gauge 215 for measuring electrical impedance as a function of bending of the gauge. Gauge 214 has end portions on the inside of each jaw and a bent portion therebetween. Impedance of gauge 215 changes as the gauge bends. Jaws 214 directly contact spaced portions of the heart wall (inside or outside) in a spaced-apart configuration, and they open and close as the heart wall expands and contracts to measure ventricular contraction. Catheter 212 also includes lumen 216 for strain gauge wires 217, energy conduit 218, and a wire 219 (alternatively optical fibers could be used for laser pulses) for connection to the rest of the energy pulse delivery system.

Figure 5G:
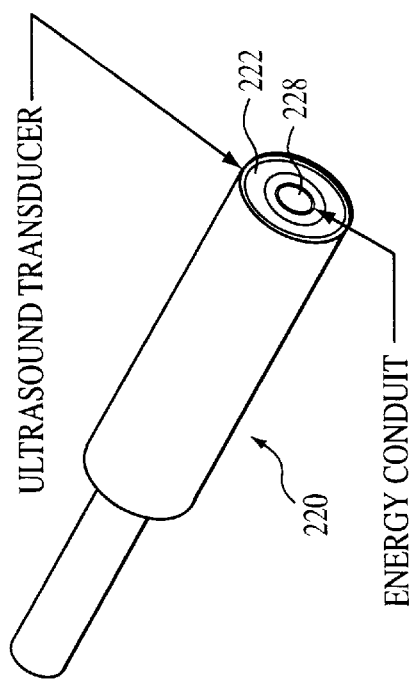
FIGS. 5G, 5H and 5I are an elevation, side view and an end view, respectively, of a myocardial revascularization catheter having an ultrasound sensor.
Figure 5I:
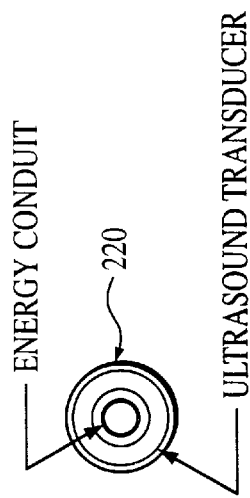
Figure 5H:
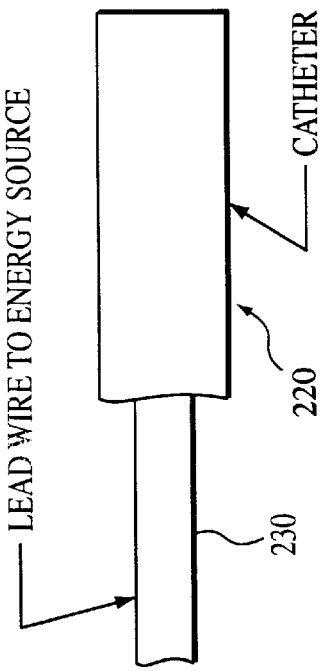

FIGS. 5G–5I show catheter 220 with ultrasound transducer 222 that senses a dimension of the myocardium of the heart (e.g., its thickness or the depth of a channel being formed). The energy pulse source 18 and the energy pulse delivery system 20 are responsive to ultrasound measurements to control the formation (e.g., the depth) of the channel. Catheter 220 also includes energy conduit 228, and a wire 230 (alternatively optical fibers could be used for laser pulses) for connection to the rest of the energy pulse delivery system.

Figure 6:
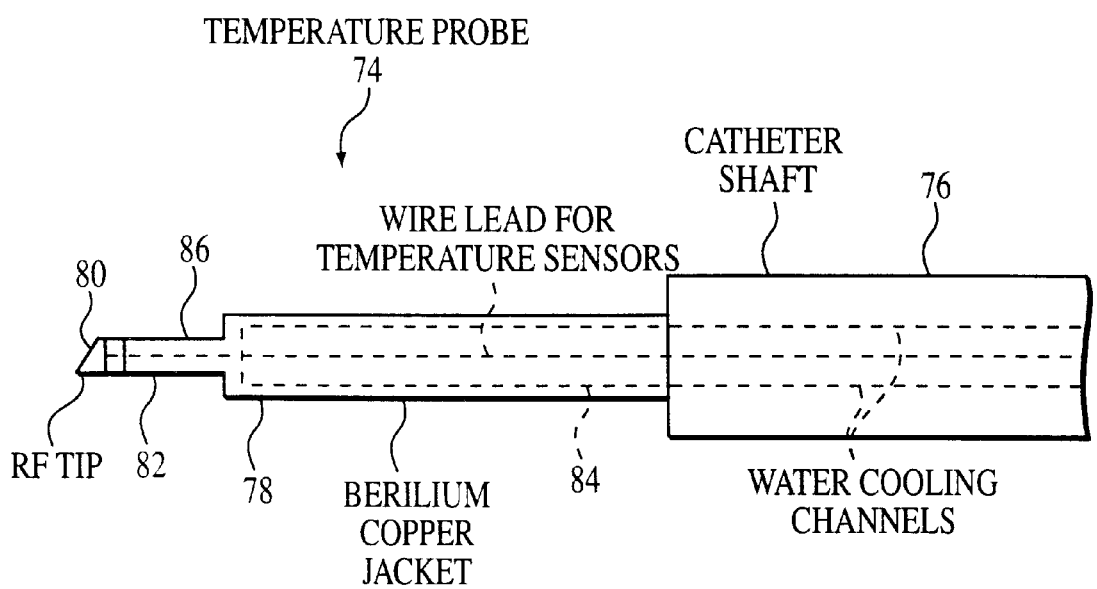
FIG. 6 is a diagrammatic side view of the end of a myocardial revascularization catheter having a temperature probe and internal cooling system.

FIG. 6 diagrammatically illustrates features of an alternative RF or microwave catheter 74, with a portion of catheter shaft 76 removed at the end to expose a beryllium copper jacket 78 thereunder. Beryllium copper jacket 78 is used to conduct heat away from tip 80 of RF or microwave needle 82 and the patient's heart tissue surrounding a channel being formed (not shown in FIG. 6). Tip 80 contains and RF or microwave electrode. Alternatively, other highly thermally conductive materials can be used for jacket 78. Jacket 78 and catheter shaft 76 include internal water channels 84 that convey cooling water to draw heat from the end of the catheter. Tip 80 contains an RF or microwave electrode for delivering RF of microwave pulses. Tip 80 of RF or microwave needle 82 also carries temperature probe 86 (corresponding to temperature sensor 22 in FIG. 1). Needle 82 is connected to be advanced by motor 40 of FIG. 2 as a channel is created in a patient's heart.

FIG. 7 shows a handpiece 90 used to direct energy pulses from energy conduit 92 to epicardial wall 94 (the external surface) of patient's heart 96. Energy conduit 92 is connected to be advanced by motor 40 of FIG. 2 as a channel is created in a patient's heart. Handpiece 90 can be used for electrical or laser pulses.

Figure 8:
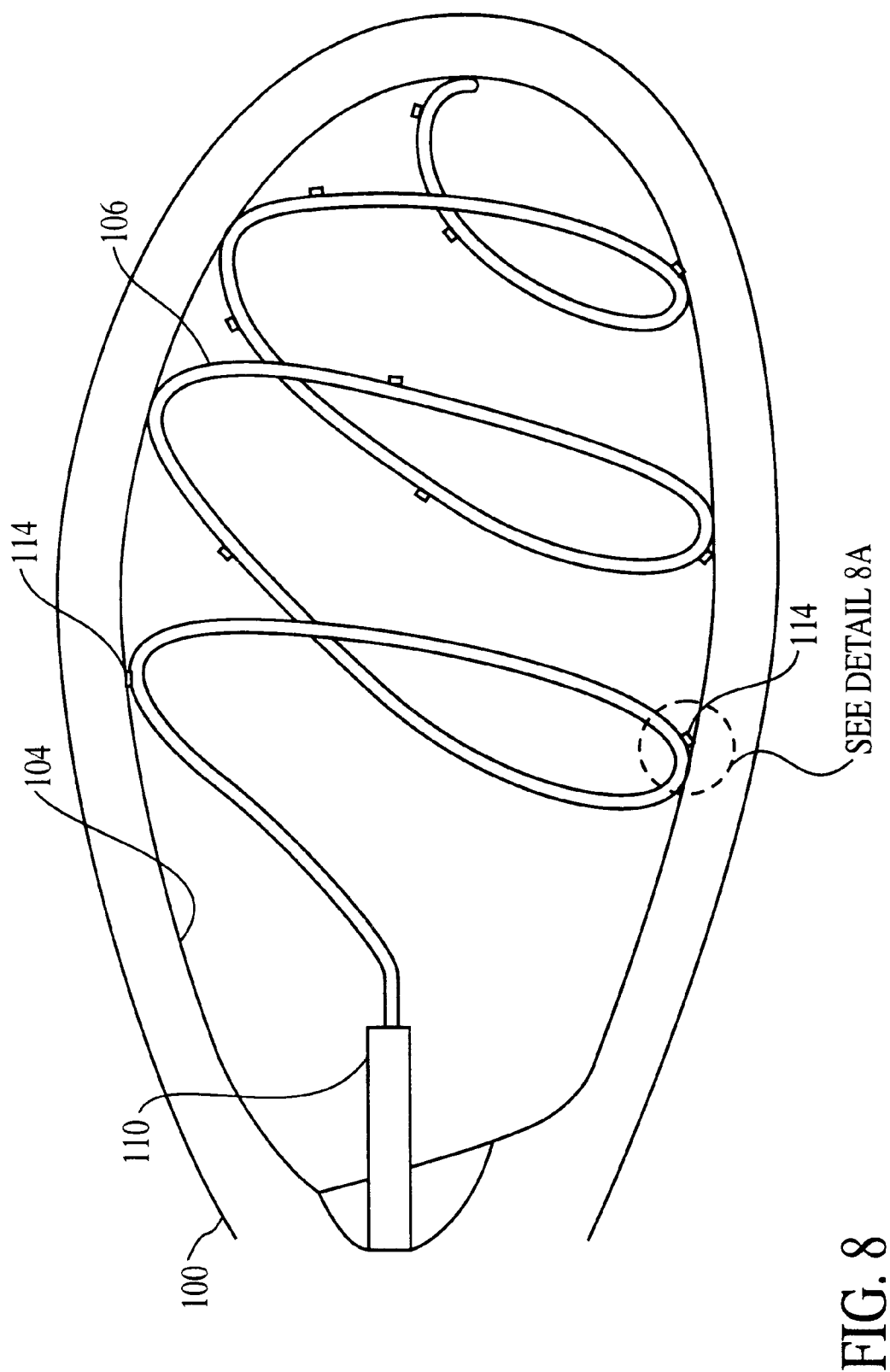
FIG. 8 is an illustration showing a spiral-type arrangement for simultaneously creating channels in a wall of a patient's heart using a plurality of RF or microwave transmitters.
Figure 8A:
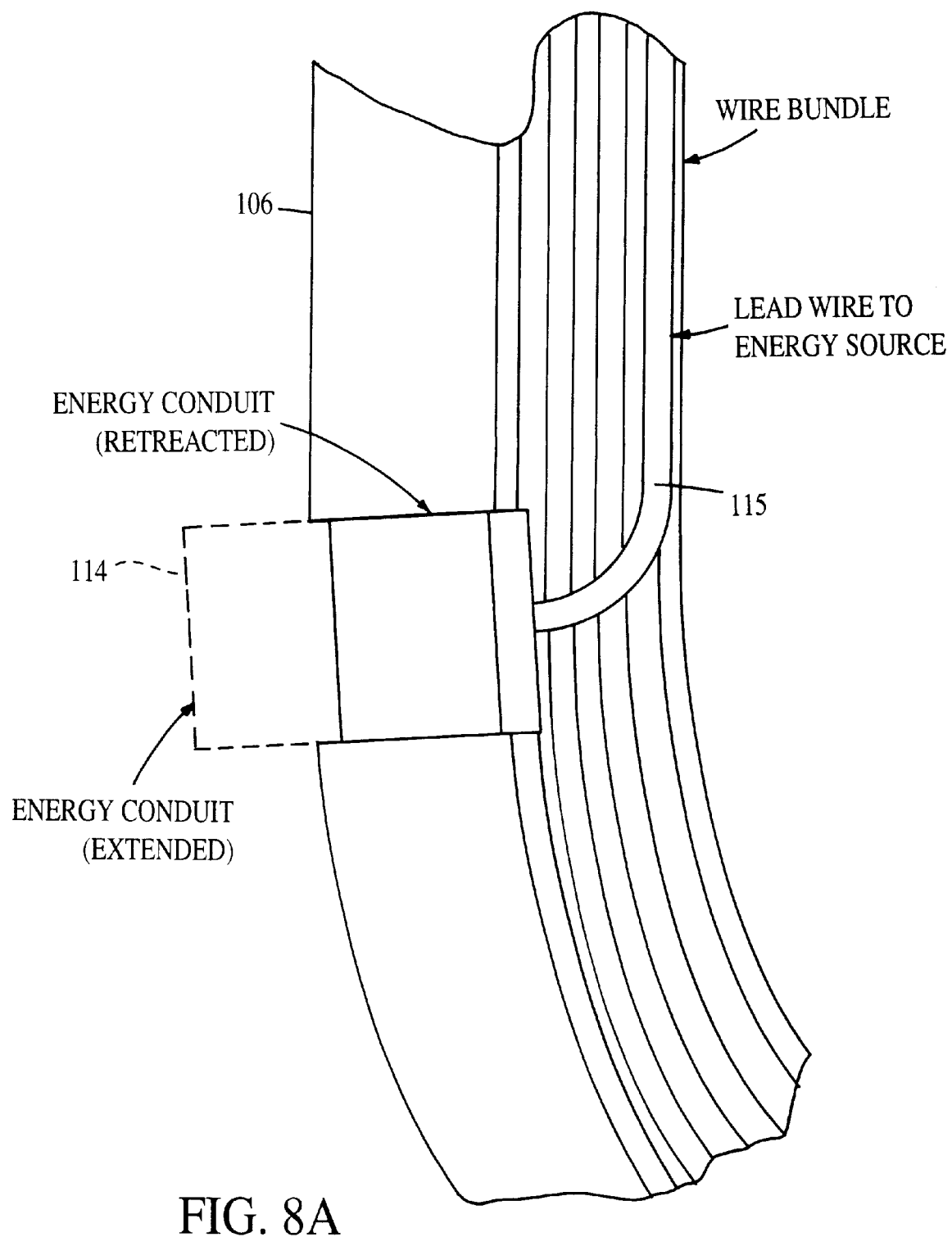
FIG. 8A is an enlarged view of a portion of FIG. 8 showing details of an energy conduit portion of the FIG. 8 device.
Figure 9:
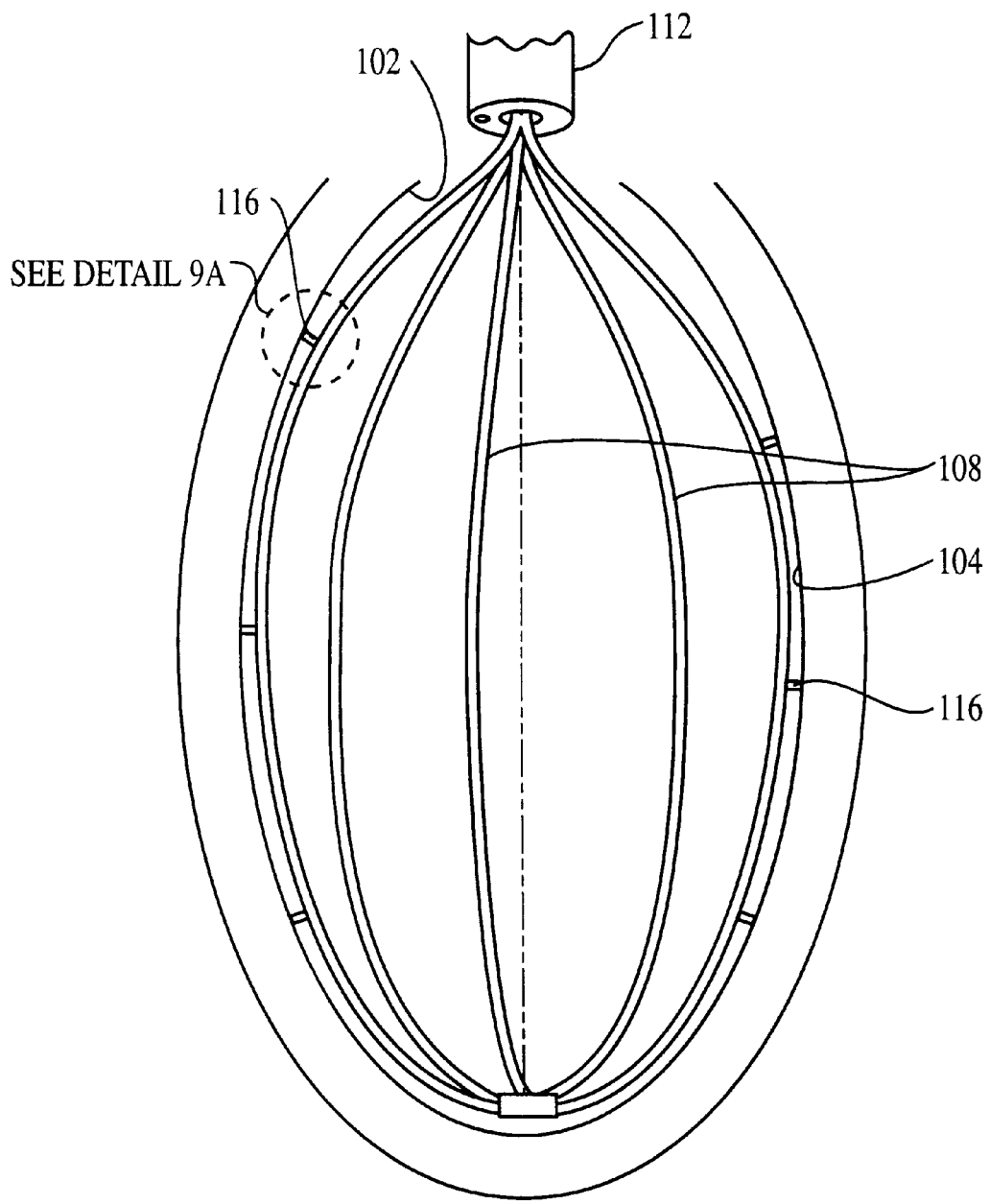
FIG. 9 is an illustration showing a basket-type arrangement for simultaneously creating channels in a wall of a patient's heart using a plurality of RF or microwave transmitters.
Figure 9A:
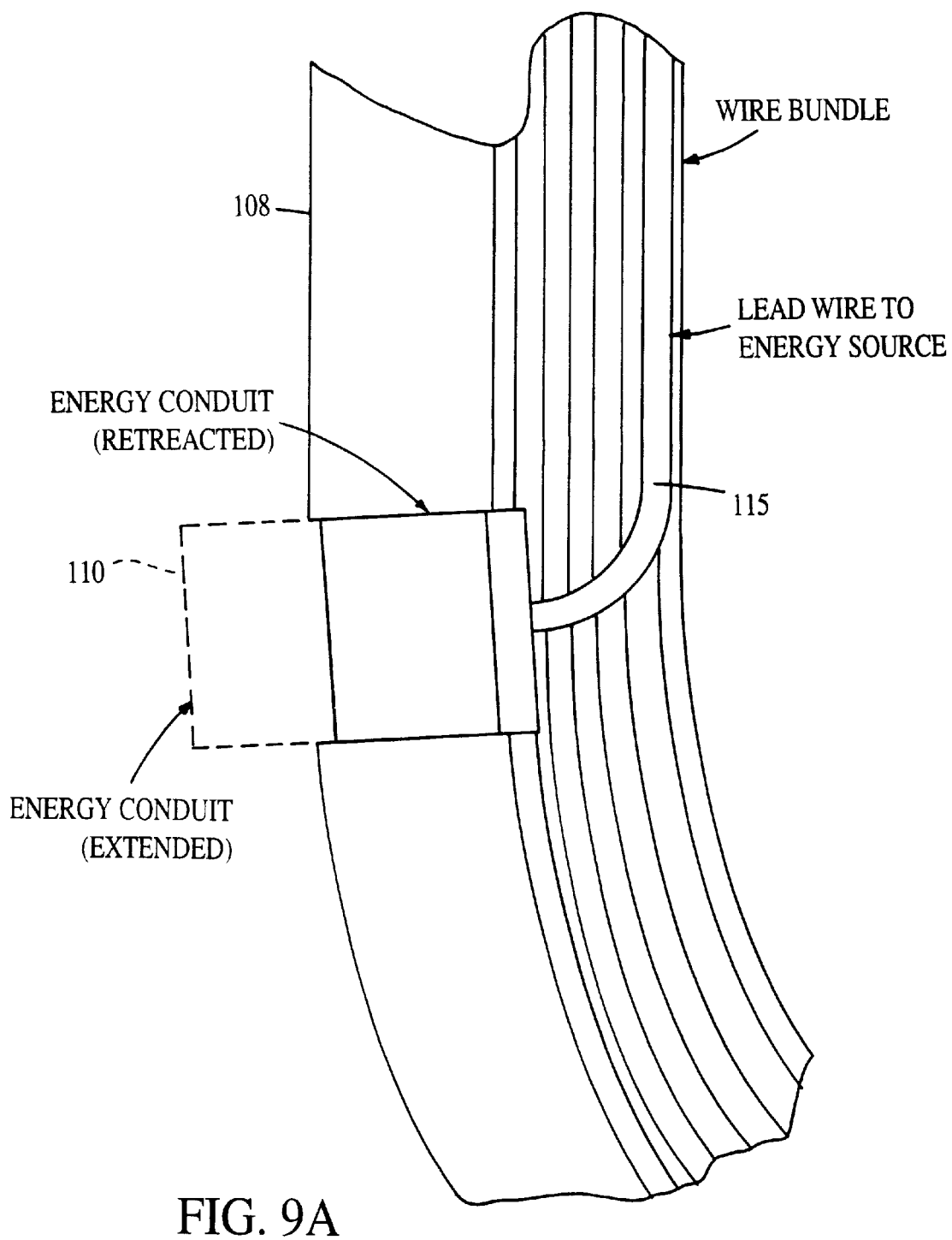
FIG. 9A is an enlarged view of a portion of FIG. 9 showing details of an energy conduit portion of the FIG. 9 device.

FIGS. 8, 8A, 9, and 9A show RF or microwave catheters 120, 112 used to simultaneously create channels at an interior surface of wall 104 of a patient's heart 100, 102. In both cases energy pulse delivery system 20 of FIG. 1 includes a support structure 106 or 108 that is expandable from a retracted position (not shown) inside catheter shafts 110, 112 to an expanded position, as shown in FIGS. 8 an 9. The support structures 106, 108 carry electrodes 114, 116 (also referred to as energy conduits) for delivering RF or microwave pulses to respective adjacent locations on wall of the heart to form respective channels in the endocardial surface 104 of the wall of the heart. Each electrode 114, 116 is connected to and driven by a main connector wire (not shown) within the support structure. The main connector wire is attached to a motion system to advance and retract the connector wire. Referring to FIG. 8A, the electrode or energy conduit 114 and electrode wires 115, which are connected to the main wire, advance and retract as the main wire is actuated. The same arrangement is also employed for the FIG. 9 support structure, as shown in FIG. 9A. The respective electrodes are advanced by motor 40 of FIG. 2 as the channels are created. In FIG. 8, support structure 106 has a spiral-like configuration. In FIG. 9, support structure 108 has a basket-like configuration.

FIGS. 10, 10A, 11 and 12 show parameters sensed by different types of heart cycle sensors 14 as a function of time; the same time scales are used for FIGS. 10–14, and FIGS. 10–12 are aligned so as to show the temporal relationship of the parameters.

Figure 10:
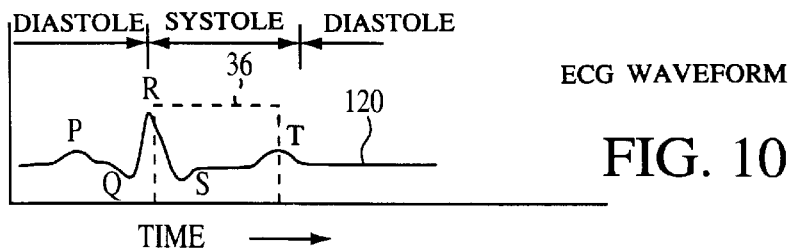
FIG. 10 is a diagram of an ECG wave useful in synchronizing the FIG. 1 system.

FIG. 10 shows waveform 120 provided by an ECG monitor. As described in U.S. Pat. No. 5,125,926, the R wave is a distinctive characteristic that can be sensed. A safe period for applying energy pulses to create channels without the risk of fibrillation is between the R and T waves, and this is indicated by the synchronization pulse 36 shown superimposed on this figure. (Another safe time period could be between the Q and the T waves.) Because FIGS. 10, 10A, 11, and 12 have their time axes aligned, safe periods corresponding to the period between the R and T waves shown on FIG. 10 can be determined with respect to the waveforms for other heart cycle parameters in FIGS. 10A–12.

Figure 10A:
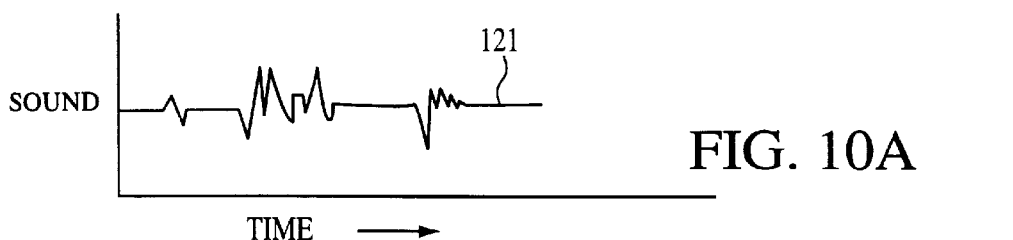
FIG. 10A is a diagram of an acoustic amplitude versus time diagram useful in synchronizing the FIG. 1 system.

FIG. 10A shows waveform 121 provided by an acoustic sensor.

Figure 11:
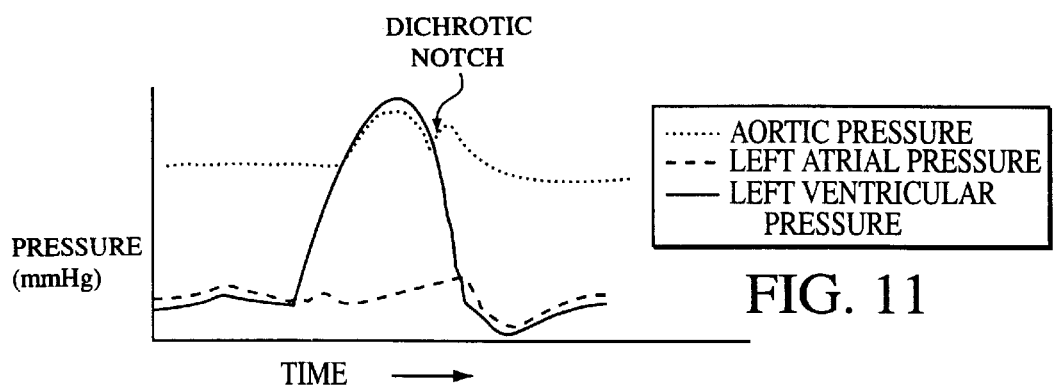
FIG. 11 is a blood pressure versus time diagram useful in synchronizing the FIG. 1 system.

FIG. 11 shows changes in blood pressure as a function of time during a heart beat cycle for arterial, ventricle and other locations. If the atrial, aortic, ventricular, or wedge bloods pressure were monitored, the slope feature of the wave could be used as a trigger event, and the safe time for directing energy pulses to the heart would be determined by the slope's direction and magnitude. For example, when the aortic slope transitions from being negative to positive, it is the beginning of the safe period. The end of the safe period would be the dichrotic notch.

Figure 12:
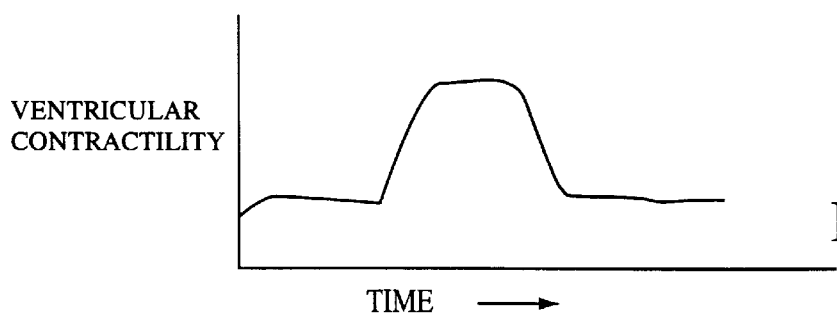
FIG. 12 is a ventricular contraction versus time diagram useful in synchronizing the FIG. 1 system

FIG. 12 shows changes in ventricle contractility as a function of time during a heart beat cycle. Contractility is sensed by electrical impedance sensors (see FIGS. 5E and 5F). The slope and/or magnitude of the wave could be used as a trigger event, and the safe time for directing energy pulses to the heart would be determined by a significant deviation in magnitude and slope.

Figure 13:
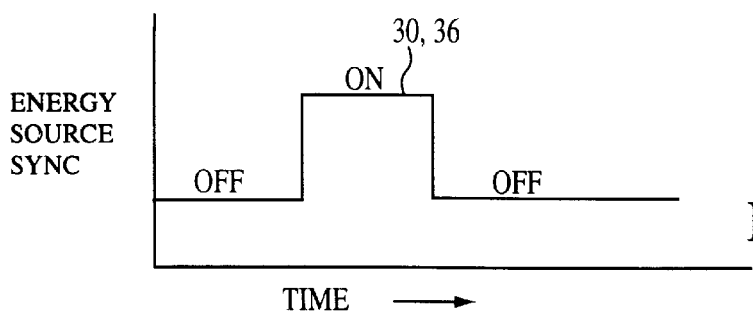
FIG. 13 is an amplitude versus time diagram showing a synchronization pulse used in synchronizing the FIG. 1 system.

FIG. 13 shows synchronization pulse 30, 36; pulse 36 is also shown superimposed on FIG. 10 in dashed lines. These pulses are generated by energy pulse system controller 16 in FIG. 1 and signal processing 34 in FIG. 2. While a single synchronization pulse 30, 36 is shown, other signals could be employed to define the beginning and end of the safe period, as discussed above with respect to synchronization signal 30 of FIG. 1.

Figure 14:
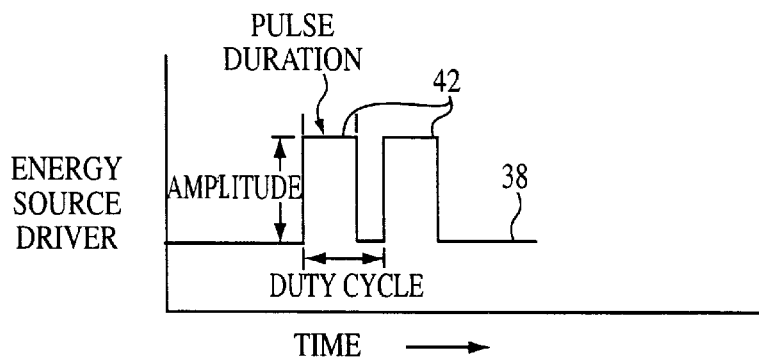
FIG. 14 is an amplitude versus time diagram showing energy pulses generated in the FIG. 1 system.

FIG. 14 shows pulse signals 42 generated by energy source driver 38 in FIG. 2. Similar or different signals could be generated by energy pulse source 18 in FIG. 1. The pulse duration, pulse amplitude, and duty cycle for pulses 42 are programmably variable by appropriate control of energy source driver 38. These parameters could additionally be varied in response to a monitored parameter such as temperature of the RF or microwave needle or heart tissue.

Energy source driver 38 also generates motor drive signal 37 (FIG. 2; not shown on FIG. 14) which controls motor 40, which advances the RF or microwave probe needle into a channel as it is being created. The beginning of this control signal can be slightly delayed with respect to the beginning of energy pulses 42, so that the probe does not puncture the tissue before tissue ablation by the energy pulses. Motor 40

(FIG. 2) is controlled to advance and retract the probe within the safe time period (generally about 100 ms) between the R and T waves in a single heartbeat cycle. In addition, driver 38 could be programmed to provide a burst that occurs as the needle is being removed from the channel to cauterize and seal the opening to the channel when energy pulses are applied to an epicardial heart surface. Also, where there might be a large number of energy pulses 42, the motor could be controlled to advance between each energy pulse, essentially into the channel portion that had just been created by the preceding energy pulse. The speed of the motor is programmably adjustable, and could additionally be varied in response to a monitored parameter such as temperature of the RF or microwave needle or tissue.

Figure 15:
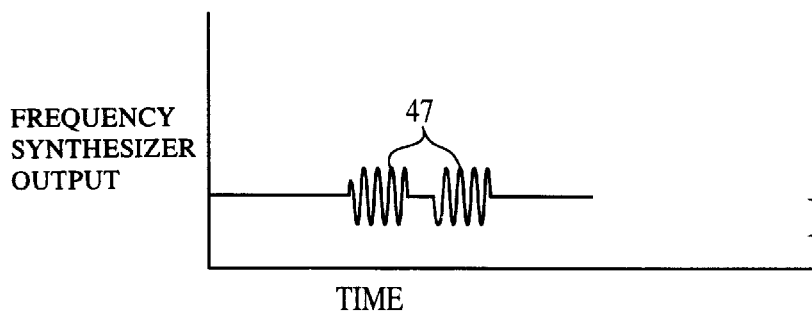
FIG. 15 is an amplitude versus time diagram illustrating an AC waveform used in the FIG. 14 pulses.

FIG. 15 illustrates the alternating current nature of the individual pulses 47 generated by frequency synthesizer 46 (FIG. 2) in response to pulses 42 (FIGS. 2, 14. Pulses 47 could have a frequency in the kilohertz to terahertz range. Preferably pulses 47 are radio frequency or microwave pulses. While a sine wave form is shown in FIG. 14, other shapes, such as square or triangular wave form shape, can be employed. The frequency is set by the energy source employed by frequency synthesizer 46. Also, the frequency could be programmably variable at synthesizer 46.

Figure 16:
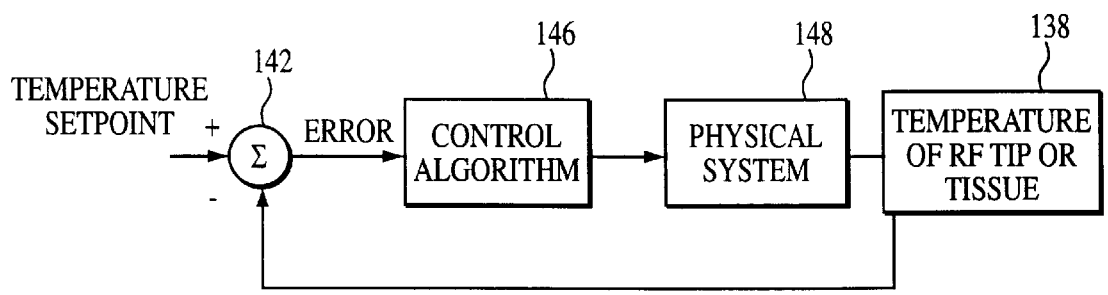
FIG. 16 is a block diagram showing a temperature control feedback loop.

FIG. 16 illustrates a control algorithm based on sensed temperature 138 of the RF or microwave needle (e.g., by temperature probe 82; FIG. 6) or adjacent heart tissue. A temperature set point 140 (e.g., provided by controller 33 based upon a user input or default condition) is provided to adder 142, along with sensed temperature 138. Adder 142 which generates error signal 144, indicating the difference between temperature set point 140 and sensed temperature 138. Error signal 144 is input to control algorithm 146, which then varies physical system 148 (e.g., components 18 and 20 of FIG. 1, components 38, 40, 46, 48 and 50 of FIG. 2, or the cooling system of FIG. 5) accordingly, so as to bring the sensed temperature 138 closer to temperature set point 140. For example, the temperature set point for tip 80 (FIG. 6) of the RF or microwave needle could be set to between 40° C. and 60° C. in order to guarantee that the tissue surrounding the channel does not exceed a safe tissue temperature to avoid denaturing of DNA and proteins. As shown in FIG. 1, temperature sensor 22 provides an output used by energy pulse source 18 to control, e.g., duration, amplitude and/or duty cycle. In the embodiment of FIG. 2, the output of the temperature sensor 22 could be provided to controller 33, which could then use it in controlling energy source driver 38 and/or RF or microwave amplifier 48. The output could also be used to control the probe cooling system (FIG. 5). In all cases, the adder 142 and control algorithm 146 can be implemented by the computer or microprocessor implementing controller 33 or other components.

In operation, heart cycle sensor 14 (FIG. 1) senses a cyclical event related to the contraction and expansion of a patient's beating heart. Such events include the ECG or other events described above and in FIGS. 10–12. Sensor 14 provides event signal 26 to energy pulse system controller 16 in FIG. 1 (signal processing 34 in FIG. 2), which generates a synchronization pulse 30 or 36 (or pulses or other signals) to energy pulse source 18 (energy source driver 38 in FIG. 2). As indicated in FIG. 10, the synchronization pulse 36 is in the safe time period between the R and T waves or within a corresponding safe time period derived from the wave forms shown in FIGS. 11 and 12. Energy pulse source 18 provides either laser pulses, electrical pulses, or other energy pulses, which are then delivered by system 20 to the patient's heart. The energy pulses create channels in the wall of the patient's heart. In the embodiments shown in FIGS. 8 and 9, multiple channels are simultaneously formed. In the other embodiments, the channels are formed one at a time, and a single catheter or handpiece is moved from one desired location to another until a sufficient number of channels have been formed. As described above, temperature of the probe or heart tissue can be monitored and used to control the delivery of energy pulses so as not to damage surrounding tissue.

Other embodiments of the invention are within the scope of the appended claims.

What is claimed is:

1. A heart-synchronized energy delivery system for performing myocardial revascularization on a beating heart of a patient comprising an energy pulse source that produces electrical pulses sufficient to create channels in a wall of said beating heart, an energy pulse delivery system connected to receive said electrical pulses and including an electrode for delivering said electrical pulses to a desired location for a channel in said wall of said beating heart, a sensor that senses a cyclical event related to the contraction and expansion of said beating heart, and an energy pulse system controller responsive to said sensor for firing said energy pulse system to provide energy to strike said beating heart only within a safe time period during a heart beat cycle, said safe time period being automatically determined by said controller with respect to said cyclical event.

2. The system of claim 1 wherein said electrical pulses are pulses of alternating current.

3. The system of claim 1 wherein said electrical pulses are pulses of alternating current at radio frequency.

4. The system of claim 1 wherein said electrical pulses are pulses of alternating current at microwave frequency.

5. The system of claim 1 wherein said sensor senses blood pressure.

6. The system of claim 1 wherein said sensor senses ventricular contraction.

7. The system of claim 1 wherein said sensor senses acoustics indicative of ventricular contraction.

8. The system of claim 1 wherein said safe time period is a period in which firing of said energy pulse system will not cause fibrillation of the heart.

9. The system of claim 1 wherein said safe time period is a period during which said heart is less sensitive electrically.

10. The system of claim 1 wherein said safe time period is within a period that corresponds to the period between the R and the T wave.

11. The system of claim 1, further comprising an electromotion mechanism for advancing said electrode into said channel as it is being formed, said mechanism advancing said electrode into new regions of said channel after the new regions have been formed.

12. The system of claim 11 wherein a plurality of said pulses are used to create each channel, and said electromotion mechanism advances each said electrode between said pulses.

13. The system of claim 1 wherein said sensor senses an electrical signal that causes said heart to beat.

14. The system of claim 13 wherein said electrical signal is an ECG signal of said beating heart, said ECG signal including Q, R, S, and T waves.

15. The system of claim 14 wherein said electrical signal is a local ECG signal, and said sensor is adapted to contact a surface of said heart.

16. The system of claim 13 wherein said electrical signal is a signal indicating a pacemaker signal.

* * * * *